United States Patent

Hennemann et al.

[11] Patent Number: 6,095,376
[45] Date of Patent: Aug. 1, 2000

[54] ANTIBACTERIAL DEVICE FOR SPRAYING A LIQUID

[75] Inventors: Pascal Hennemann, Eu; Frédéric Prost, Paris; Jean-Louis Bougamont, Eu, all of France

[73] Assignee: SOFAB, France

[21] Appl. No.: 09/147,058

[22] PCT Filed: Mar. 27, 1997

[86] PCT No.: PCT/FR97/00550

§ 371 Date: Sep. 29, 1998

§ 102(e) Date: Sep. 29, 1998

[87] PCT Pub. No.: WO97/36690

PCT Pub. Date: Oct. 9, 1997

[30] Foreign Application Priority Data

Mar. 29, 1996 [FR] France .................................. 96 03943

[51] Int. Cl.[7] .............................. B67D 5/58; G01F 11/30
[52] U.S. Cl. ...................... 222/190; 222/321.6; 222/380
[58] Field of Search ........................ 222/189.06, 189.09, 222/189.11, 321.1, 321.6, 378, 420, 190, 380

[56] References Cited

U.S. PATENT DOCUMENTS 4,437,592  3/1984  Bon ..................................... 222/402.12
4,830,284  5/1989  Maerte .................................... 222/321
5,195,665  3/1993  Lina ....................................... 222/380
5,360,145  11/1994  Gueret .................................... 222/321
5,490,938  2/1996  Sawan et al. ........................... 222/420

FOREIGN PATENT DOCUMENTS 898320  6/1962  United Kingdom .

Primary Examiner—Gregory L. Huson
Assistant Examiner—Keats Quinalty
Attorney, Agent, or Firm—Bacon & Thomas PLLC

[57] ABSTRACT

An antibacterial spray device is provided for spraying a liquid contained in a receptacle (R). The device comprises an endpiece designed to cover an outlet tube (G) of a pump (P) which is mounted on the receptacle (R) by a collar (C). The endpiece (1) includes an internal duct (11) which extends from the outlet tube (G) to an end cavity (10) and is surrounded coaxially by a tapering cylindrical outside wall (12), which is attached at its bottom portion to a bearing shoulder (13) for operating the pump (P). The end cavity (10) is provided with an ejection orifice (100) and houses a valve (2) therein. All component parts that come into contact with the liquid, including the endpiece, are made, at least in part, of a plastics material containing between 0.2% and 2% by weight of a bactericidal agent which acts solely by coming into contact with the liquid but without being released into the liquid.

9 Claims, 4 Drawing Sheets

ANTIBACTERIAL DEVICE FOR SPRAYING A LIQUID

BACKGROUND OF THE INVENTION

1. Field of the Invention

The present invention relates to an antibacterial spray device for spraying a liquid.

2. Description of the Related Art

A liquid is contained in a receptacle and spraying thereof is generally performed using a conventional device comprising, in particular, an endpiece designed to cover an outlet tube of a Pump Which IS mounted on the receptacle by a collar.

Such a device is described, for example, in U.S. Pat. No. 4,830,284 where the endpiece includes an internal duct which extends from the outlet tube to an end cavity and is surrounded coaxially by a tapering cylindrical outside wall, which is attached at its bottom portion to a bearing shoulder for operating the pump. The end cavity is provided with an ejection orifice and houses a valve.

In such devices, the liquid is protected against bacteria only by the valves of tile pump. Where appropriate, further protection is provided by enclosing the liquid in a deformable pouch which is bonded to the pump or by using a receptacle of variable volume which is provided with a movable base.

However, these protection means are not sufficiently effective to keep tile packaging sterile or to prevent the liquid from becoming contaminated.

Another bacterial protection technique consists of incorporating a chemical preservative in the liquid itself.

However, such preservatives result in a change in the quality of the liquid, which is especially disadvantageous for pharmaceuticals and cosmetics where undesirable side effects for the user may be generated.

SUMMARY OF THE INVENTION

The object of the present Invention is to resolve the abovementioned technical problems by combing mechanical sealing means with an antibacterial agent.

According to the invention, this object is achieved by a spray device for spraying a liquid contained in a receptacle, the device comprising an endpiece designed to cover an outlet tube of a pump which is mounted on the receptacle by a collar. The endpiece includes an internal duct which extends from the outlet tube to an end cavity and is surrounded coaxially by a tapering cylindrical outside wall, which is attached at its bottom portion to a bearing shoulder for operating the pump. The end cavity is provided with an ejection orifice and houses a valve. The internal duct is of annular section, about a solid axial rod. The end cavity is closed and is defined inside the endpiece by a front wall thereof, which is pierced by the ejection orifice, and by a downstream longitudinal end of the axial rod. All component parts that come into contact with the liquid, including the endpiece, are made, at least in part, of a plastics material containing between 0.2% and 2% by weight of a bactericidal agent which acts solely by coming into contact with the liquid but without being released into the liquid.

In a particular embodiment, the bactericidal agent is a compound containing silver in ionic form.

According to an advantageous characteristic, the shoulder of the endpiece is extended by a bottom cylindrical sleeve which ensures that the endpiece is axially guided inside a neck of the receptacle and comes into abutment with the collar of the pump.

The shoulder preferably has a span which is greater than an outside diameter of the neck of the receptacle. As such, the shoulder preferably extends radially outwardly in at least two directions beyond the outside diameter.

According to another characteristic, the valve is removable and is constituted by a solid cylindrical body which is provided at its base with an elastically-deformable peripheral lip which bears against internal side walls of the cavity and is oriented towards the ejection orifice.

In a first variant, the internal duct is central and axial.

In such case, the end cavity is open and is defined inside the endpiece by the annular rim of the internal duct.

The valve is thus held in the end cavity by a nozzle which closes a mouth of the end cavity, at least in part.

The nozzle preferably includes a front face, which is pierced by a central ejection orifice, and a side skirt having a bottom edge, which is provided with a locking member for locking the nozzle in the end cavity.

In the device of the invention, antibacterial protection is ensured by mechanical elements only without the chemical composition of the liquid being modified.

The end valve provides effective further sealing of the device by forming a protective barrier which is in addition to that provided by the pump valves.

The bactericidal action is ensured by a chemical agent which is present in the plastics material at least constituting the endpiece. The agent is not released into the liquid and it only acts by coming into contact the liquid when the liquid passes into the endpiece, or into any other component part of the device where the agent is present.

In the presence of bacterial pollution, the various valves of the device (in the endpiece and the pump) create a degree of sealing which is capable of stopping the pollution from spreading before it reaches the liquid. In turn, the bactericidal agent completely eliminates the pollution at the point where it is stopped.

Molding the endpiece out of a plastics material containing a bactericidal agent makes the device hygienic. If the endpiece is put into contact with bacterial contamination, its surface is polluted. The presence of the bactericidal agent thus destroys the polluting bacteria and keeps the endpiece sterile by avoiding any new contamination.

The present invention therefore results from combining mechanical sealing means with bactericidal chemical means.

BRIEF DESCRIPTION OF THE DRAWINGS

The invention will be better understood on reading the following description, accompanied by the drawings, in which.

DETAILED DESCRIPTION OF THE PREFERRED EMBODIMENTS

Figure 1:
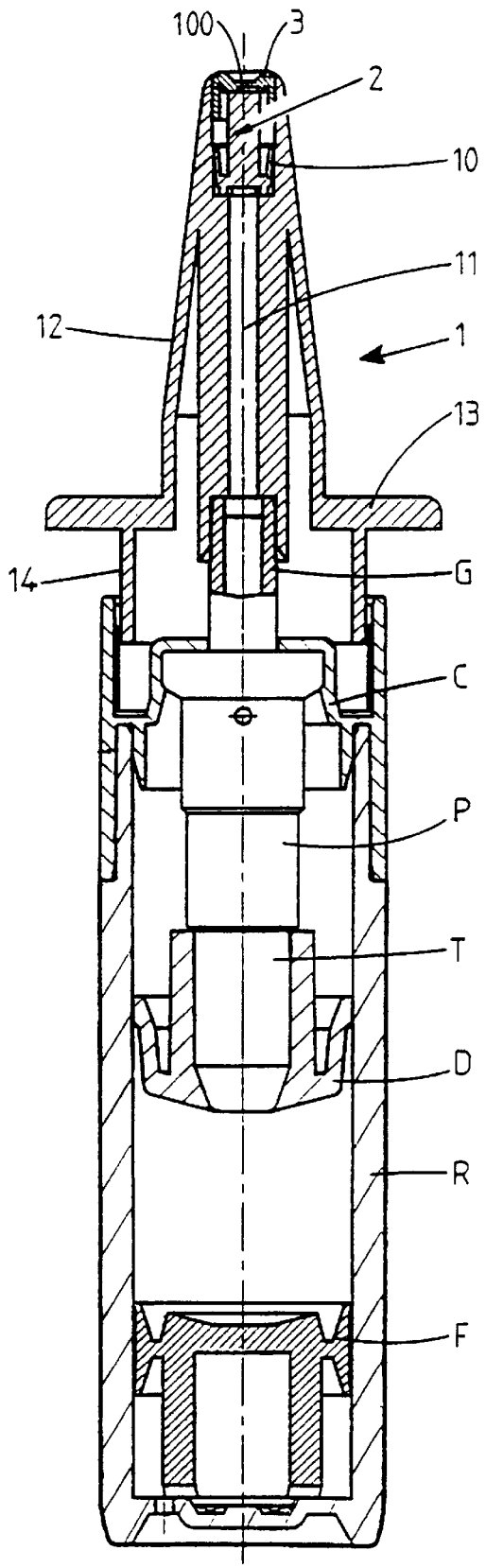
FIG. 1 is a cross-section view of a first embodiment of the invention.

FIG. 1 is a cross-section view of a first embodiment of the device of the invention, comprising a receptacle R containing a liquid, a pump P which is mounted in sealed manner on the receptacle R by a collar C and fitted with an outlet tube G which is designed to be covered by an endpiece 1. The receptacle R further includes a movable base F, while a foot T of the pump P is fitted with a bush D which cooperates with the base F in order to empty the receptacle R.

Figure 3A:
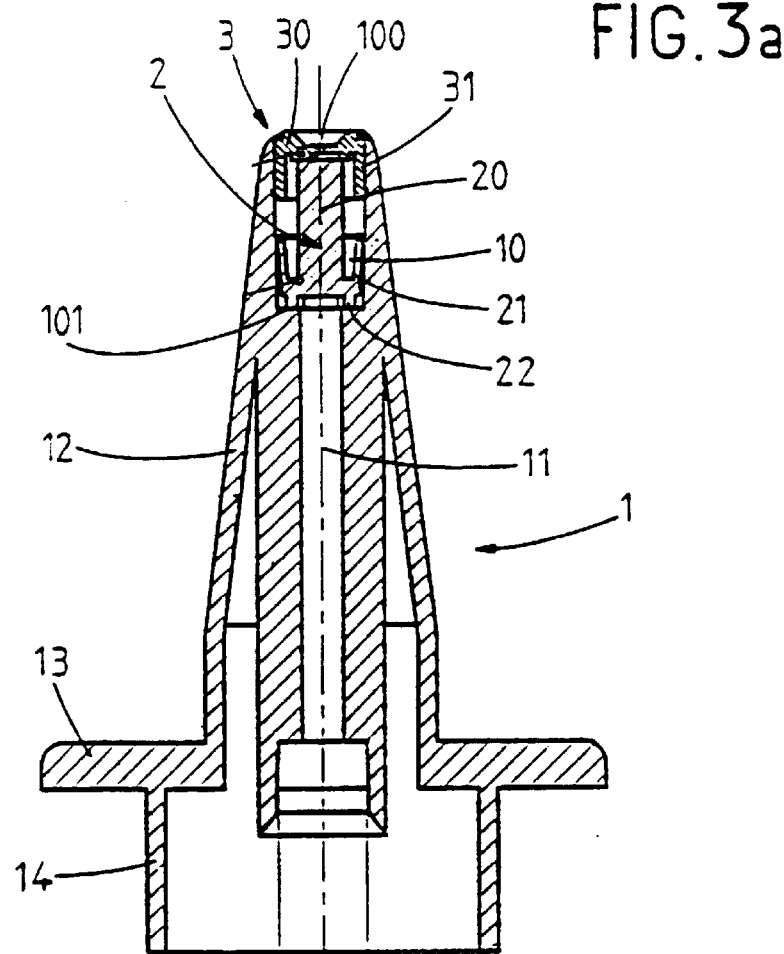
FIGS. 3a and 3b are large-scale views in cross-section and from above, respectively, of the embodiment of FIGS. 1 and 2.
Figure 3B:
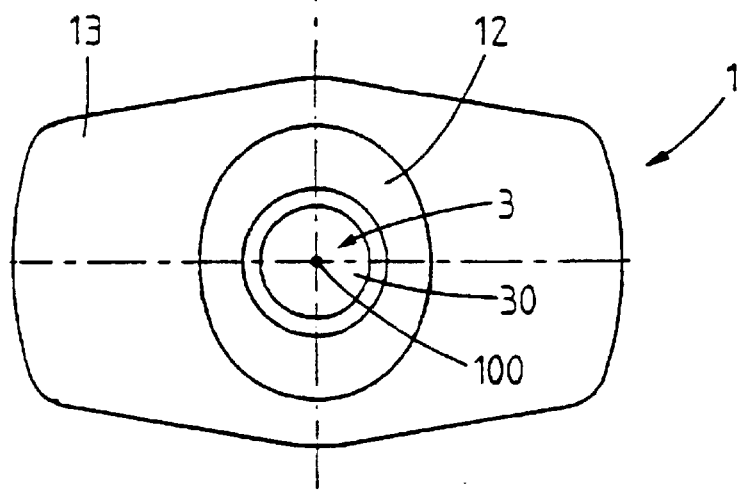

In general, the endpiece I includes an internal duct 11 which extends from the outlet tube G to an end cavity 10, which is provided with an ejection orifice 100 and which houses a valve 2, as shown in FIGS. 3a, 3b.

The internal duct 11 is surrounded coaxially by a tapering cylindrical outside wall 12 which is attached at its bottom portion to a shoulder 13 which extends transversely (radially outwardly) and which is designed to be pressed manually in order to operate the pump P.

The shoulder 13 is provided with a bottom cylindrical sleeve 14 which ensures that the endpiece 1 is axially guided inside the neck of the receptacle R and comes into abutment with the collar C of the pump P.

The shoulder 13 has a span which is greater than the outside diameter of the neck R of the receptacle so as to provide an effective bearing surface. In particular, the shoulder 13 extends radially outwardly beyond the outside diameter in at least two directions.

In accordance with the invention, the endpiece 1 is made of a plastics material containing a bactericidal agent, at least where the internal walls of the duct 11, the cavity 10, and the valve 2 are in contact with the liquid.

Naturally, the endpiece 1 may be made entirely of a bactericidal plastics material.

In the case where the endpiece is injection or compression molded, the bactericidal agent may be mixed with the bactericidal agent before molding.

All the component parts of the device (i.e. the endpiece 1, the body, the piston, and the outlet of the pump P, the receptacle R, the collar C . . .) may also be made of a bactericidal plastics material so as to reinforce this action.

The bactericidal agent is preferably a compound containing silver, e.g. silver in ionic form.

The bactericidal agent acts only by coming into contact with the liquid. For this reason, it is essential for all zones of the endpiece 1 and, where appropriate, of the spray device as a whole, which come into contact with the liquid, to contain a sufficient quantity of bactericidal agent.

The quantity which is considered to be effective in the field of the liquids under consideration lies in the range 0.2% and 2% by weight of antibacterial agent in the plastics material.

By way of example, such a material makes it possible to cause an initial bacterial population of the Aureus staphylococcus type of 105 to decrease in a logarithmic manner and in 24 hours to a final population of less than $10^2$.

Figure 2:
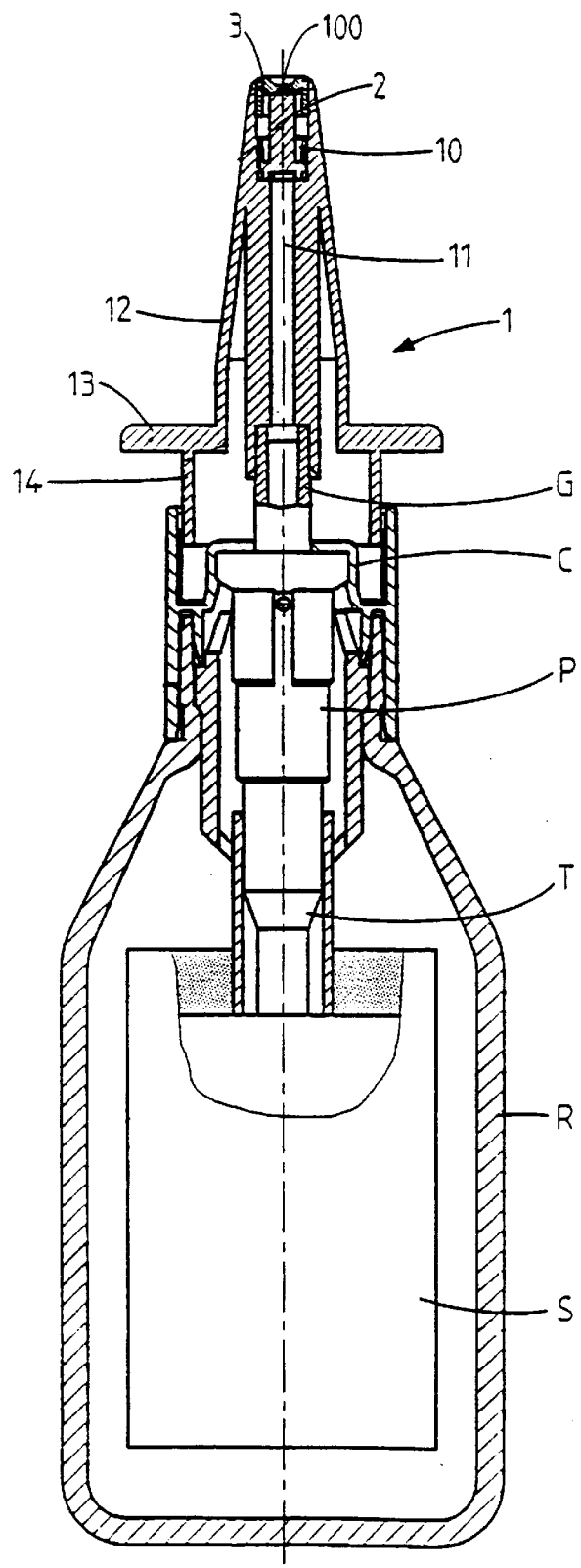
FIG. 2 is a cross-section view of a variant of the embodiment of FIG. 1.

FIG. 2 shows a cross-section view of a second embodiment, in which the receptacle R contains a flexible deformable pouch S which is bonded to the foot T of the pump P.

Here, the embodiment of the endpiece 1 is identical to that of FIGS. 1 and 3a, 3b.

In the first embodiment, the internal duct 11 is central and axial. It opens out at its top end into the cavity 10 which receives the valve 2 in a removable manner.

Here, the cavity 10 is open and is defined inside the endpiece 1 by an annular rim 101 of the internal duct 11.

The valve 2 is constituted by a solid cylindrical body 20 which is provided at its base with an elastically-deformable peripheral lip 21 which bears against internal side walls of the cavity 10.

The peripheral lip 21 is oriented towards the ejection orifice 100 situated at the 10 opening of the cavity 10.

By operating the pump P, the liquid is put under pressure and escapes via the outlet tube G towards the ejection orifice 100 via the internal duct 11, thereby deforming the peripheral lip 21 of the valve 2 in the cavity 10.

The lip 21 is deformed by being pushed towards the cylindrical body 20 of the valve 2, thereby freeing a side passage for the liquid.

The valve 2 is held in the cavity 10 by a nozzle 3 which closes a mouth of the cavity 10, at least in part.

The nozzle 3 includes a dish-shaped front face 30, which is pierced by a central ejection orifice for ejecting the liquid, and a side skirt 31 having a bottom edge which is provided with a locking member for locking the nozzle in the cavity 10.

Figure 4A:
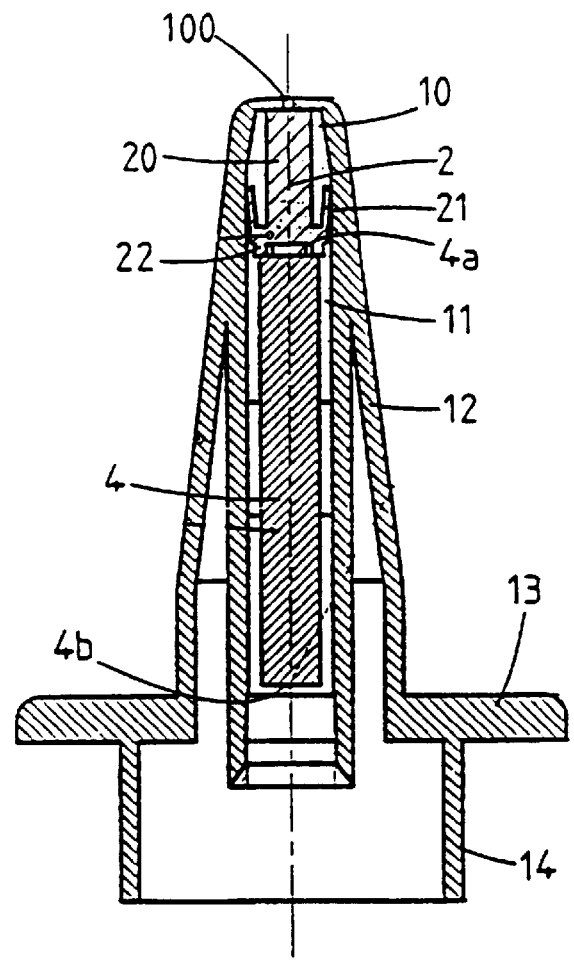
FIGS. 4a and 4b are views in cross-section and from above, respectively, of another embodiment of the invention.
Figure 4B:
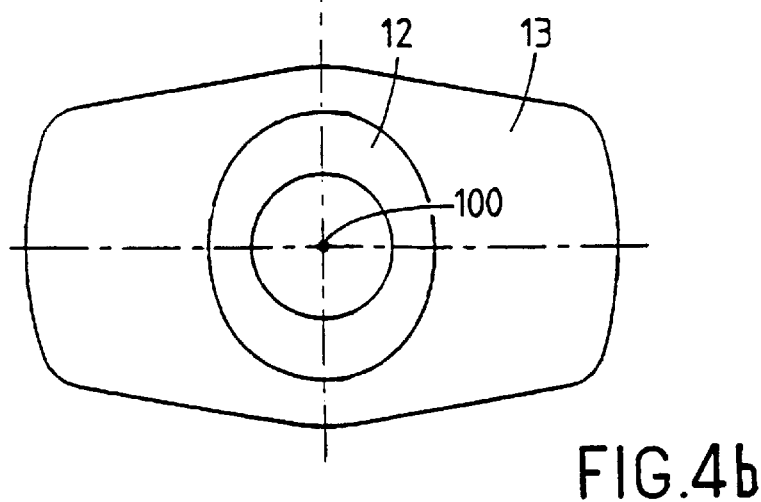

In the embodiment of FIGS. 4a and 4b, the internal duct 11 is of annular section, about a removable, solid axial rod 4. In this case, the cavity 10 is closed and is defined inside the endpiece 1 by its front wall, which is pierced by the ejection orifice 100, and by a downstream longitudinal end 4a of the removable axial rod 4.

The valve 2 is always removable. It is inserted into the cavity 10 via the duct 11 and is held by force against the inside face of the front wall of the endpiece 1 by the rod 4. Where appropriate, the rod 4 is secured at its downstream end 4a by the valve 2. The upstream longitudinal end 4b of the rod 4 is disposed, when the valve is in a mounting position, at a distance from the opening of the outlet tube G, so as to allow the liquid to escape.

What is claimed is:

1. An antibacterial spray device for spraying a liquid contained in a receptacle (R), the device comprising:

a pump (P) which is mounted on the receptacle (R) by a collar (C), the pump (P) having an outlet tube (G);

an endpiece (1) designed to cover the outlet tube (G) of the pump (P), the endpiece (1) including an internal duct (11) and a closed end cavity (10), the internal duct (11) extending from the outlet tube (G) to the closed end cavity (10) and being of annular section about an axial rod (4), the axial rod (4) having a downstream longitudinal end (4a), the closed end cavity (10) being defined inside the endpiece (1) by a front wall thereof and the downstream longitudinal end (4a) of the axial rod (4), the front wall being pierced by an ejection orifice (100);

a tapering cylindrical outside wall (12) which coaxially surrounds the internal duct (11), the tapering cylindrical outside wall (12) being attached at a bottom portion thereof to a bearing shoulder (13) for operating the pump (P); and a valve (2) housed in the closed end cavity (10);

wherein all component parts that come into contact with the liquid, including the endpiece (1), are made, at least in part, of a plastics material containing between 0.2% and 2% by weight of a bactericidal agent which acts solely by coming into contact with the liquid but without being released into the liquid.

2. A device according to claim 1, wherein the bactericidal agent is a compound containing silver in ionic form.

3. A device according to claim 1, wherein the shoulder (13) of the endpiece (1) is extended by a bottom cylindrical sleeve (14) which ensures that the endpiece (1) is axially guided inside the neck of the receptacle (R) and comes into abutment with the collar (C) of the pump (P).

4. A device according to claim 1, wherein the shoulder (13) of the endpiece (1) extends radially outwardly in at least two directions substantially beyond an outside diameter of a neck of the receptacle (R).

5. A device according to claim 1, wherein the valve (2) is removable and is constituted by a solid cylindrical body (20), the solid cylindrical body (20) being provided at a base thereof with an elastically-deformable peripheral lip (21) which bears against internal side walls of the closed end cavity (10) and is oriented towards the ejection orifice (100).

6. An antibacterial spray device for spraying a liquid contained in a receptacle (R), the device comprising:

a pump (P) which is mounted on the receptacle (R) by a collar (C), the pump (P) having an outlet tube (G);

an endpiece (1) designed to cover the outlet tube (G) of the pump (P), the endpiece (1) including an internal duct (11) and an end cavity (10), the internal duct (11) extending from the outlet tube (G) to the end cavity (10) and being central and axial;

a tapering cylindrical outside wall (12) which coaxially surrounds the internal duct (11), the tapering cylindrical outside wall (12) being attached at a bottom portion thereof to a bearing shoulder (13) for operating the pump (P); and a valve (2) housed in the end cavity (10);

wherein all component parts that come into contact with the liquid, including the endpiece (1), are made, at least in part, of a plastics material containing between 0.2% and 2% by weight of a bactericidal agent which acts solely by coming into contact with the liquid but without being released into the liquid.

7. A device according to claim 6, wherein the end cavity (10) is open and is defined inside the endpiece (1) by an annular rim (101) of the internal duct (11).

8. A device according to claim 7, further comprising:

a nozzle (3) which closes a mouth of the open end cavity (10), at least in part, such that the valve (2) is held in the end cavity (10) by the nozzle (3).

9. A device according to claim 8, wherein the nozzle (3) comprises:

a front face (30) which is pierced by a central ejection orifice; and a side skirt (31) having a bottom edge which is provided with a locking member for locking the nozzle (3) in the end cavity (10).

* * * * *